US011636842B2

(12) United States Patent
Carlile et al.

(10) Patent No.: US 11,636,842 B2
(45) Date of Patent: Apr. 25, 2023

(54) EAR-MOUNTABLE LISTENING DEVICE HAVING A MICROPHONE ARRAY DISPOSED AROUND A CIRCUIT BOARD

(71) Applicant: Iyo Inc., Redwood City, CA (US)

(72) Inventors: Simon Carlile, Sydney (AU); Jason Rugolo, Mountain View, CA (US)

(73) Assignee: Iyo Inc., Redwood City, CA (US)

( * ) Notice: Subject to any disclaimer, the term of this patent is extended or adjusted under 35 U.S.C. 154(b) by 72 days.

(21) Appl. No.: 17/162,674

(22) Filed: Jan. 29, 2021

(65) Prior Publication Data

US 2022/0246128 A1 Aug. 4, 2022

(51) Int. Cl.
*A61F 11/06* (2006.01)
*G10K 11/16* (2006.01)
*H03B 29/00* (2006.01)
*G10K 11/178* (2006.01)
*H04R 1/10* (2006.01)

(52) U.S. Cl.
CPC .. *G10K 11/17827* (2018.01); *G10K 11/17885* (2018.01); *H04R 1/1016* (2013.01); *H04R 1/1041* (2013.01); *G10K 2210/1081* (2013.01); *G10K 2210/1082* (2013.01)

(58) Field of Classification Search
CPC ........ G10K 11/17827; G10K 11/17885; H04R 1/1016; H04R 1/1041
See application file for complete search history.

(56) References Cited

U.S. PATENT DOCUMENTS 6,068,589 A 5/2000 Neukermans
6,069,958 A * 5/2000 Weisel .................. H04R 3/005 381/56
8,204,263 B2 6/2012 Pedersen et al.
8,630,431 B2 1/2014 Gran
9,510,112 B2 11/2016 Petersen et al.
10,142,745 B2 11/2018 Petersen et al.
2002/0001389 A1 1/2002 Amiri et al.
2004/0001137 A1 * 1/2004 Cutler .................. H04N 5/2259 348/14.09
2006/0067548 A1 3/2006 Slaney et al.
(Continued)

FOREIGN PATENT DOCUMENTS

EP 3062528 A1 8/2016
GB 2364121 A 1/2002
(Continued)

OTHER PUBLICATIONS

International Search Report and Written Opinion, PCT App. No. PCT/US22/14151, dated May 13, 2022, 10 pages.

*Primary Examiner* — Simon King
(74) *Attorney, Agent, or Firm* — Nicholson Devos Webster & Elliott

(57) ABSTRACT

An ear-mountable listening device includes an array of microphones physically arranged into a ring pattern to capture sounds from an environment and output first audio signals that are representative of the sounds captured by the microphones. A speaker is arranged to emit audio into an ear in response to a second audio signal. Electronics are coupled to the array of microphones and the speaker and configured to capture the sounds with the array of microphones to generate the first audio signals and generate the second audio signal that drives the speaker based upon one or more of the first audio signals.

21 Claims, 9 Drawing Sheets

(56) References Cited

U.S. PATENT DOCUMENTS

| | | | | |
|---|---|---|---|---|
| 2007/0223748 | A1* | 9/2007 | Wang | H04R 5/023 381/301 |
| 2010/0195842 | A1* | 8/2010 | Sibbald | G10K 11/17861 381/71.6 |
| 2011/0137209 | A1 | 6/2011 | Lahiji et al. | |
| 2012/0076316 | A1* | 3/2012 | Zhu | H04R 3/005 381/71.11 |
| 2013/0101141 | A1* | 4/2013 | McElveen | H04R 1/406 381/123 |
| 2014/0119553 | A1 | 5/2014 | Usher et al. | |
| 2015/0055796 | A1* | 2/2015 | Nugent | H04M 3/5125 381/92 |
| 2016/0080867 | A1* | 3/2016 | Nugent | H04R 1/02 381/26 |
| 2016/0323668 | A1* | 11/2016 | Abraham | H04R 31/00 |
| 2017/0332186 | A1* | 11/2017 | Riggs | H04S 7/301 |
| 2018/0197527 | A1 | 7/2018 | Guiu et al. | |
| 2020/0177986 | A1 | 6/2020 | Wen | |
| 2020/0213711 | A1 | 7/2020 | Rugolo et al. | |
| 2020/0296492 | A1* | 9/2020 | McElveen | H04R 29/005 |
| 2020/0396555 | A1 | 12/2020 | Cartwright et al. | |

FOREIGN PATENT DOCUMENTS

| | | | |
|---|---|---|---|
| JP | 2005-109942 | A | 4/2005 |
| KR | 10-1753064 | B1 | 7/2017 |
| WO | 2012018641 | A2 | 2/2012 |
| WO | 2019/048355 | A1 | 3/2019 |

* cited by examiner

EAR-MOUNTABLE LISTENING DEVICE HAVING A MICROPHONE ARRAY DISPOSED AROUND A CIRCUIT BOARD

TECHNICAL FIELD

This disclosure relates generally to ear mountable listening devices.

BACKGROUND INFORMATION

Ear mounted listening devices include headphones, which are a pair of loudspeakers worn on or around a user's ears. Circumaural headphones use a band on the top of the user's head to hold the speakers in place over or in the user's ears. Another type of ear mounted listening device is known as earbuds or earpieces and include individual monolithic units that plug into the user's ear canal.

Both headphones and ear buds are becoming more common with increased use of personal electronic devices. For example, people use headphones to connect to their phones to play music, listen to podcasts, place/receive phone calls, or otherwise. However, headphone devices are currently not designed for all-day wearing since their presence blocks outside noises from entering the ear canal without accommodations to hear the external world when the user so desires. Thus, the user is required to remove the devices to hear conversations, safely cross streets, etc.

Hearing aids for people who experience hearing loss are another example of an ear mountable listening device. These devices are commonly used to amplify environmental sounds. While these devices are often worn all day, they often fail to accurately reproduce environmental cues, thus making it difficult for wearers to localize reproduced sounds. As such, hearing aids also have certain drawbacks when worn all day in a variety of environments.

With any of the above ear mountable listening devices, monolithic implementations are common. These monolithic designs are not easily custom tailored to the end user, and if damaged, require the entire device to be replaced at greater expense.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system, apparatus, and method of operation for an ear-mountable listening device are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1A:
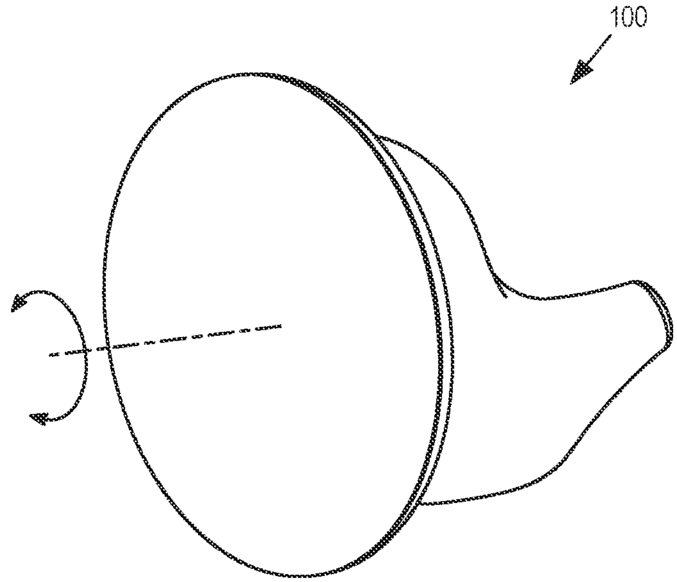
FIG. 1A is a frontal perspective illustration of an ear-mountable listening device, in accordance with an embodiment of the disclosure.
Figure 1B:
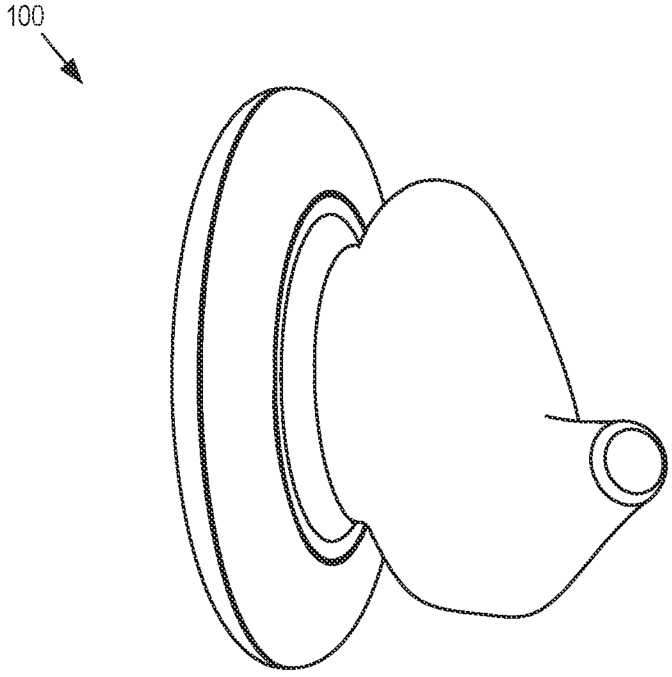
FIG. 1B is a rear perspective illustration of the ear-mountable listening device, in accordance with an embodiment of the disclosure.
Figure 1C:
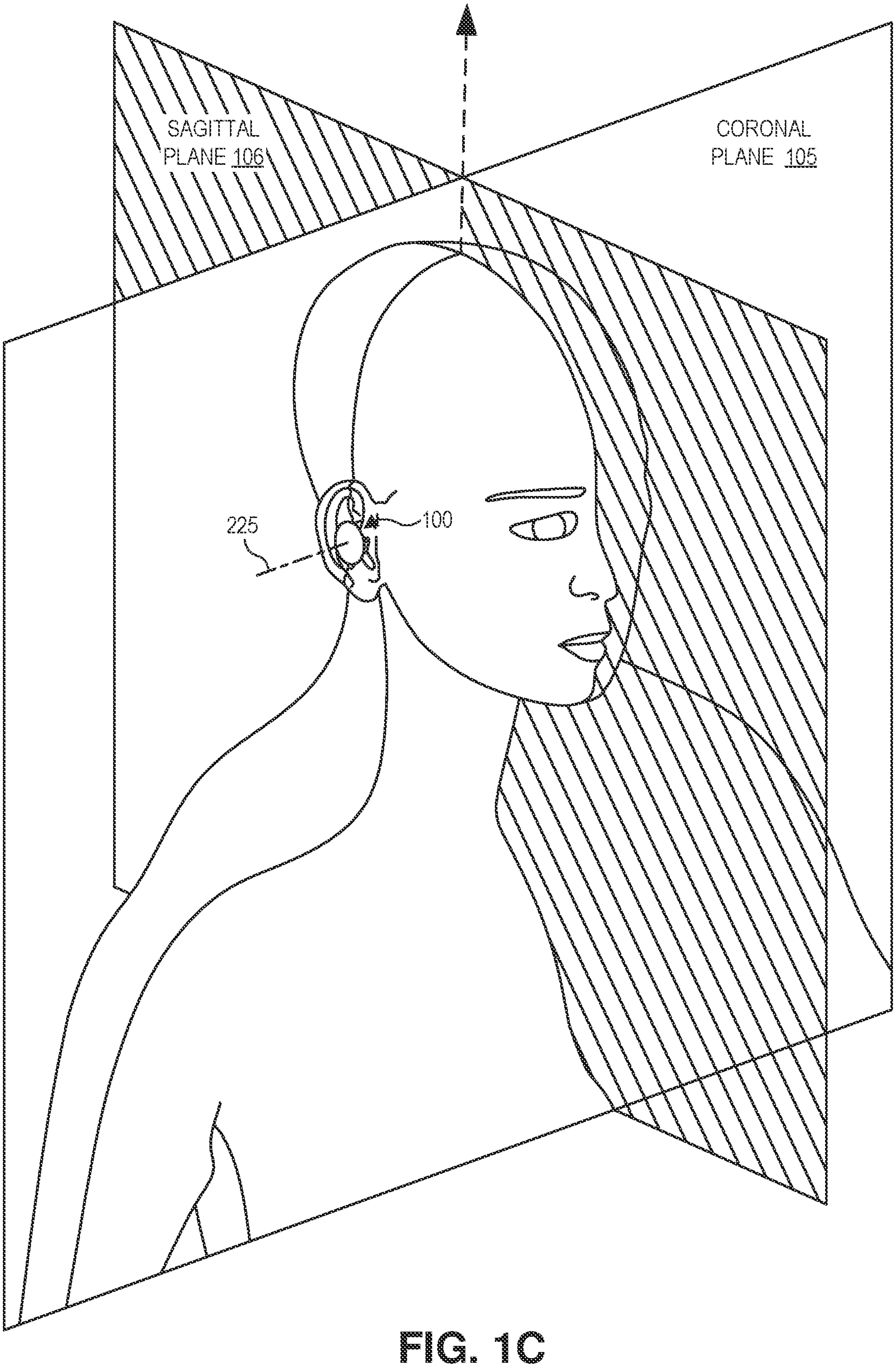
FIG. 1C illustrates the ear-mountable listening device when worn in an ear, in accordance with an embodiment of the disclosure.

FIGS. 1A-C illustrate an ear-mountable listening device 100, in accordance with an embodiment of the disclosure. In various embodiments, ear-mountable listening device 100 is capable of facilitating a variety auditory functions including wirelessly connecting to (and/or switching between) a number of audio sources (e.g., Bluetooth connections to personal computing devices, etc.) to provide in-ear audio to the user, controlling the volume of the real world (e.g., modulated noise cancellation and transparency), providing speech hearing enhancements, localizing environmental sounds, and even rendering auditory virtual objects (e.g., auditory assistant or other data sources as speech or auditory icons). Ear-mountable listening device 100 is amenable to all day wearing. When the user desires to block out external environmental sounds, the mechanical design and form factor along with active noise cancellation can provide substantial external noise dampening (e.g., 40 to 50 dB). When the user desires a natural auditory interaction with their environment, ear-mountable listening device 100 can provide near (or perfect) perceptual transparency by reinforcing the user's natural Head Related Transfer Function (HRTF), thus maintaining spaciousness of sound and the ability to localize sound origination in the environment. When the user desires auditory aid or augmentation, ear-mountable listening device 100 may be capable of acoustical beamforming to dampen or nullify deleterious sounds while enhancing others. The auditory enhancement may be spatially aware and capable of amplitude and/or spectral enhancements to facilitate specific user functions (e.g., enhance a specific voice frequency originating from a specific direction while dampening other background noises). In some embodiments, machine learning principles may even be applied to sound segregation and signal reinforcement.

Figure 2:
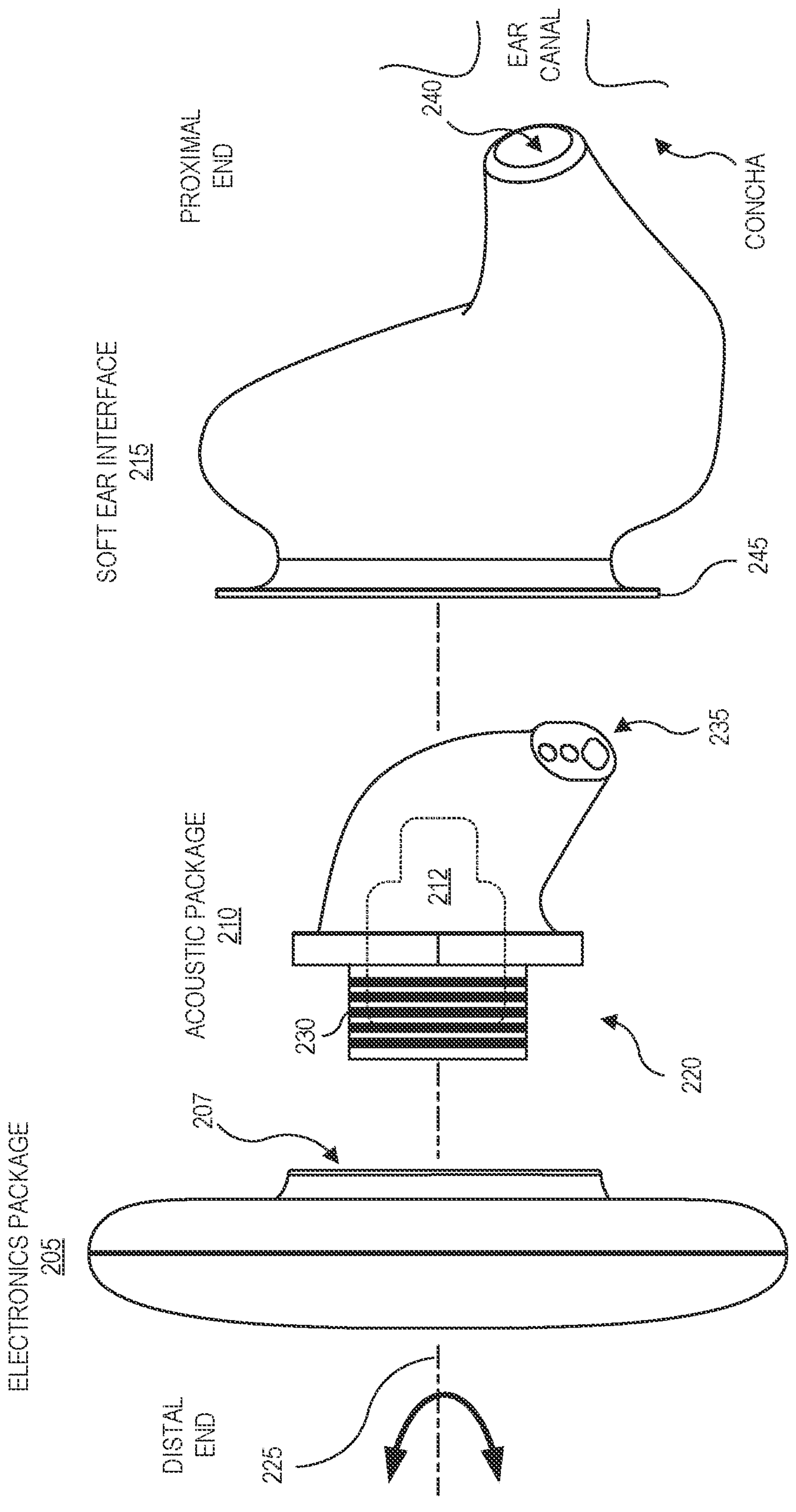
FIG. 2 is an exploded view illustration of the ear-mountable listening device, in accordance with an embodiment of the disclosure.

Referring to FIG. 2, ear-mountable listening device 100 has a modular design including an electronics package 205, an acoustic package 210, and a soft ear interface 215. The three components are separable by the end-user allowing for any one of the components to be individually replaced should it be lost or damaged. The illustrated embodiment of electronics package 205 has a puck-like shape and includes an array of microphones for capturing external environmental sounds along with electronics disposed on a main circuit board for data processing, signal manipulation, communications, user interfaces, and various sensors. In some embodiments, the main circuit board has an annular disk shape with a central hole.

The illustrated embodiment of acoustic package 210 includes one or more speakers 212, and in some embodiments, an internal microphone for capturing user noises incident via the ear canal, and electromechanical components of a rotary user interface. A distal end of acoustic package 210 includes a cylindrical post 220 that slides into and couples with a cylindrical port 207 on the proximal side of electronics package 205. In embodiments where the main circuit board within electronics package 205 is an annular disk, cylindrical port 207 aligns with the central hole (e.g., see FIG. 6). The annular shape of the main circuit board and cylindrical port 207 facilitate a compact stacking of speaker (s) 212 with a microphone array of electronics package 205 directly in front of the opening to the ear canal enabling a more direct orientation of speaker 212 to the axis of the auditory canal.

Post 220 may be held mechanically and/or magnetically in place while allowing electronics package 205 to be rotated about central axial axis 225 relative to acoustic package 210 and soft ear interface 215. In one embodiment, the mechanical/magnetic connection facilitates rotational detents (e.g., 8, 16, 32) that provide a force feedback as the user rotates electronic package 205 with their fingers. Electrical trace rings 230 disposed circumferentially around post 220 provide electrical contacts for power and data signals communicated between electronics package 205 and acoustic package 210. In other embodiments, post 220 may be eliminated in favor of using flat circular disks to interface between electronics package 205 and acoustic package 210.

Soft ear interface 215 is fabricated of a flexible material (e.g., silicon, flexible polymers, etc.) and has a shape to insert into a concha and ear canal of the user to mechanically hold ear-mountable listening device 100 in place (e.g., via friction or elastic force fit). Soft ear interface 215 may be a custom molded piece (or fabricated in a limited number of sizes) to accommodate different concha and ear canal sizes/shapes. Soft ear interface 215 provides a comfort fit while mechanically sealing the ear to dampen or attenuate direct propagation of external sounds into the ear canal. Soft ear interface 215 includes an internal cavity shaped to receive a proximal end of acoustic package 210 and securely holds acoustic package 210 therein, aligning ports 235 with in-ear aperture 240. A flexible flange 245 seals soft ear interface 215 to the backside of electronics package 205 encasing acoustic package 210 and keeping moisture away from acoustic package 210. Though not illustrated, in some embodiments, the distal end of acoustic package 210 may include a barbed ridge encircling ports 235 that friction fit or "click" into a mating indent feature within soft ear interface 215.

FIG. 1C illustrates how ear-mountable listening device 100 is held by, mounted to, or disposed in the user's ear. As illustrated, soft ear interface 215 is shaped to hold ear-mountable listening device 100 with central axial axis 225 substantially falling within (e.g., within 20 degrees) a coronal plane 105. As is discussed in greater detail below, an array of microphones extends around central axial axis 225 in a ring pattern that substantially falls within a sagittal plane 106 of the user. Furthermore, when ear-mountable listening device 100 is worn, electronics package 205 is held close to the pinna of the ear and aligned along or within the pinna plane. Holding electronics package 205 close into the pinna not only provides a desirable industrial design (relative to further out protrusions), but may also has less impact on the user's HRTF or more readily lend itself to a definable/characterizable impact on the user's HRTF, for which offsetting calibration may be achieved. As mentioned, the central hole in the main circuit board along with cylindrical port 207 facilitate the close in mounting of electronics package 205 despite mounting speakers 212 directly in front of the ear canal in between electronics package 205 and the ear canal along central axial axis 225.

Figure 3:
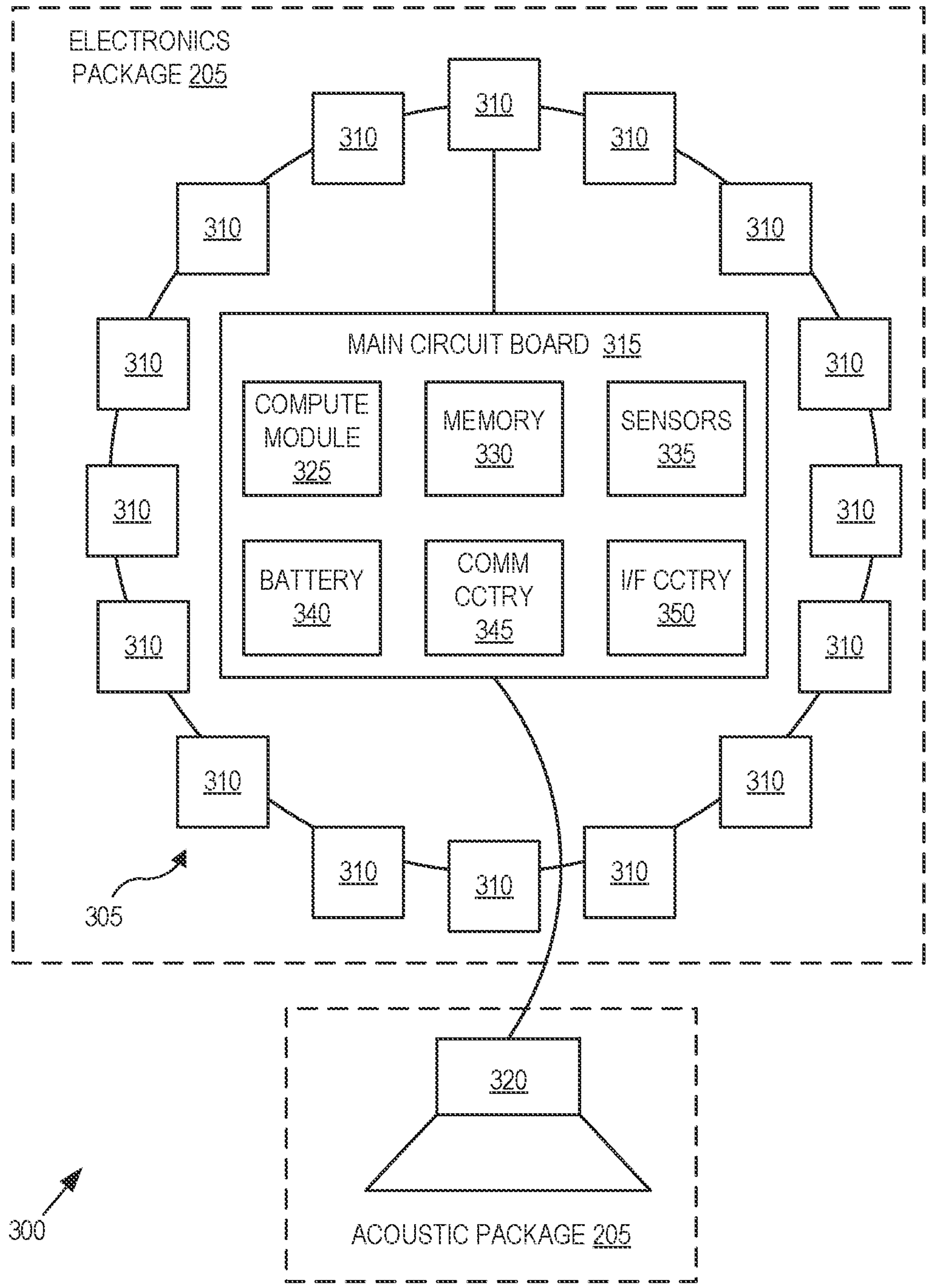
FIG. 3 is a block diagram illustrating select functional components of the ear-mountable listening device, in accordance with an embodiment of the disclosure.

FIG. 3 is a block diagram illustrating select functional components 300 of ear-mountable listening device 100, in accordance with an embodiment of the disclosure. The illustrated embodiment of components 300 includes an array 305 of microphones 310 and a main circuit board 315 disposed within electronics package 205 while speaker(s) 320 are disposed within acoustic package 205. Main circuit board 315 includes various electronics disposed thereon including a compute module 325, memory 330, sensors 335, battery 340, communication circuitry 345, and interface circuitry 350. Although not illustrated, acoustic package 205 may also include some electronics for digital signal processing (DSP), such as a printed circuit board (PCB) containing a signal decoder and DSP processor for digital-to-analog (DAC) conversion and EQ processing, a bi-amped crossover, and various auto-noise cancellation and occlusion processing logic.

In one embodiment, microphones 310 are arranged in a ring pattern (e.g., circular array, elliptical array, etc.) around a perimeter of main circuit board 315. Main circuit board 315 itself may have a flat disk shape, and in some embodiments be an annular disk with a central hole. There are a number of advantages to mounting multiple microphones 320 about a flat disk on the side of the user's head for an ear-mountable listening device. However, one limitation of such an arrangement is that the flat disk restricts what can be done with the space occupied by the disk. This becomes a significant limitation if it is necessary or desirable to orientate a loudspeaker, such as speaker 320 (or speakers 212), on axis with the auditory canal as this may push the flat disk (and thus electronics package 205) quite proud of the ears. In the case of a binaural listening system, protrusion of electronics package 205 significantly out past the pinna plane may even distort the natural time of arrival of the sounds to each ear and further distort spatial perception and the user's HRTF potentially beyond a calibratable correction. Fashioning the disk as an annulus (or donut) enables protrusion of the driver of speaker 320 (or speakers 212) through main circuit board 315 and thus a more direct orientation/alignment of speaker 320 with the entrance of the auditory canal.

Microphones 310 may each be disposed on their own individual microphone substrates. The microphone port of each microphone 310 may be spaced in substantially equal angular increments about central axial axis 225. In FIG. 3, sixteen microphones 310 are equally spaced; however, in other embodiments, more or less microphones may be distributed in the ring pattern about central axial axis 225.

Compute module 325 may include a programmable microcontroller that executes software/firmware logic stored in memory 330, hardware logic (e.g., application specific integrated circuit, field programmable gate array, etc.), or a combination of both. Although FIG. 3 illustrates compute module 325 as a single centralized resource, it should be appreciated that compute module 325 may represent multiple compute resources disposed across multiple hardware elements on main circuit board 315 and which interoperate to collectively orchestrate the operation of the other functional components. For example, compute module 325 may execute logic to turn ear-mountable listening device 100 on/off, monitor a charge status of battery 340 (e.g., lithium ion battery, etc.), pair and unpair wireless connections, switch between multiple audio sources, execute play, pause, skip, and volume adjustment commands received from interface circuitry 350, commence multi-way communication sessions (e.g., initiate a phone call via a wirelessly coupled phone), control volume of the real-world environment passed to speaker 320 (e.g., modulate noise cancellation and perceptual transparency), enable/disable speech enhancement modes, enable/disable smart volume modes (e.g., adjusting max volume threshold and noise floor), or otherwise. In one embodiment, compute module 325 includes a trained neural network.

Sensors 335 may include a variety of sensors such as an inertial measurement unit (IMU) including one or more of a three axis accelerometer, a magnetometer (e.g., compass), or a gyroscope. Communication interface 345 may include one or more wireless transceivers including near-field magnetic induction (NFMI) communication circuitry and antenna, ultra-wideband (UWB) transceivers, a WiFi transceiver, a radio frequency identification (RFID) backscatter tag, a Bluetooth antenna, or otherwise. Interface circuitry 350 may include a capacitive touch sensor disposed across the distal surface of electronics package 205 to support touch commands and gestures on the outer portion of the puck-like surface, as well as a rotary user interface (e.g., rotary encoder) to support rotary commands by rotating the puck-like surface of electronics package 205. A mechanical push button interface operated by pushing on electronics package 205 may also be implemented.

Figure 4:
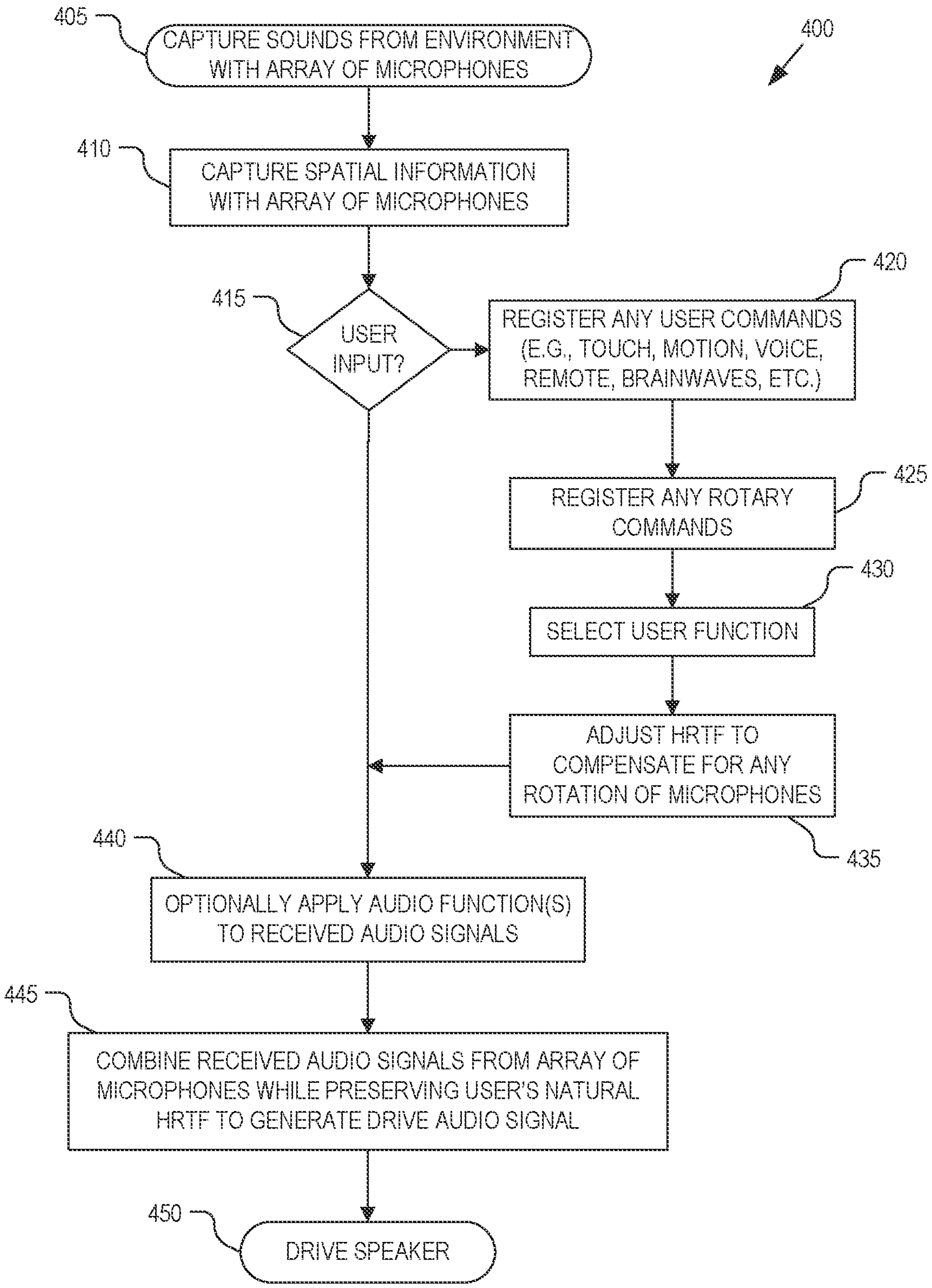
FIG. 4 is a flow chart illustrating operation of the ear-mountable listening device, in accordance with an embodiment of the disclosure.

FIG. 4 is a flow chart illustrating a process 400 for operation of ear-mountable listening device 400, in accordance with an embodiment of the disclosure. The order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

In a process block 405, sounds from the external environment incident upon array 305 are captured with microphones 310. Due to the plurality of microphones 310 along with their physical separation, the spaciousness or spatial information of the sounds is also captured (process block 410). By organizing microphones 310 into a ring pattern (e.g., circular array) with equal angular increments about central axial axis 225, the spatial separation of microphones 310 is maximized for a given area thereby improving the spatial information that can be extracted by compute module 325 from array 305.

Spatial information includes the diversity of amplitudes and phase delays across the acoustical frequency spectrum of the sounds captured by each microphone 310 along with the respective positions of each microphone. In some embodiments, the number of microphones 310 along with their physical separation (both within a single ear-mountable listening device and across a binaural pair of ear-mountable listening devices worn together) can capture spatial information with sufficient spatial diversity to localize the origination of the sounds within the user's environment. Compute module 325 can use this spatial information to recreate an audio signal for driving speaker(s) 320 that preserves the spaciousness of the original sounds (in the form of phase delays and amplitudes applied across the audible spectral range). In one embodiment, compute module 325 is a neural network trained to leverage the spatial information and reinforce, or otherwise preserve, the user's natural HRTF so that the user's brain does not need to relearn a new HRTF when wearing ear-mountable listening device 100. While the human mind is capable of relearning new HRTFs within limits, such training can take over a week of uninterrupted learning. Since a user of ear-mountable listening device 100 would be expected to wear the device some days and not others, or for only part of a day, preserving/reinforcing the user's natural HRTF can be important so as not to disorientate the user and reduce the barrier to adoption of a new technology.

In a decision block 415, if any user inputs are sensed, process 400 continues to process blocks 420 and 425 where any user commands are registered. User commands may include touch commands, motion commands (e.g., head motions sensed with an IMU), voice commands, commands received wirelessly from an external remote, brainwave commands sensed via brainwave a brainwave sensor, etc (process block 420). As discussed above, the touch commands may be received as touch gestures on the distal surface of electronics package 205 while rotary commands may be received via the user rotating electronics package 205. The touch commands may be sensed using a capacitive touch sensing sensor disposed over electronics package 205 under a protective mesh layer. User commands also include rotary commands (process block 425). The rotary commands may be determined using the IMU to sense each rotational detent. Alternatively (or additionally), array 305 may be used to sense the rotational orientation of electronics package 205 and thus implement the rotary encoder. For example, the user's own voice originates from a known fixed location relative to the user's ears. As such, the array of microphones 310 may be used to perform acoustical beamforming to localize the user's voice and determine the absolute rotational orientation of array 305. Since the user may not be talking when operating the rotary interface, the acoustical beamforming and localization may be a periodic calibration while the IMU or other rotary encoders are used for instantaneous registration of rotary motion. Upon registering a user command, compute module 325 selects the appropriate function, such as volume adjust, skip/pause song, accept or end phone call, enter enhanced voice mode, enter active noise cancellation mode, enter acoustical beam steering mode, or otherwise (process block 430). Although not illustrated in FIG. 4, user commands may be sensed via other mechanisms. For example, the IMU may be used to detect various head motions, microphone array 305, or an internal microphone, may detect voice commands, wireless communication 345 may be used to receive commands from a handheld remote, or even electrodes may be used to detect brain wave patterns.

Once the user rotates electronics package 205, the angular position of each microphone 310 in array 305 is changed. This requires rotational compensation or transformation of the HRTF to maintain meaningful state information of the spatial information captured by array 305. Accordingly, in process block 435, compute module 325 applies the appropriate rotational transformation matrix to compensate for the new positions of each microphone 310. Again, in one embodiment, input from IMU may be used to apply an instantaneous transformation and acoustical beamforming techniques may be used to apply a periodic recalibration when the user talks. In the case of using acoustical beamforming to determine the absolute angular position of array 305, the maximum number of detents in the rotary interface is related to the number of microphones 310 in array 305 to enable angular position disambiguation for each of the detents using acoustical beamforming.

In a process block 440, the audio data and/or spatial information captured by array 305 may be used by compute module 325 to apply various audio processing functions (or implement other user functions selected in process block 430). For example, the user may rotate electronics package 205 to designate an angular direction for acoustical beamforming. This angular direction may be selected relative to the user's front to position a null lobe (for selectively muting an unwanted sound) or a maxima lobe (for selectively amplifying a desired sound). Other audio functions may include filtering spectral components to enhance a conversation, adjusting the amount of active noise cancellation, etc.

In a process block 445, one or more of the audio signals captured by array 305 are intelligently combined to generate an audio signal for driving speaker(s) 320 (process block 450). The audio signals output from array 305 may be combined and digitally processed to implement the various processing functions. For example, compute module 325 may analyze the audio signals output from each microphone 310 to identify one or more "lucky microphones." Lucky microphones are those microphones that due to their physical position happen to acquire an audio signal with less noise than the others (e.g., sheltered from wind noise). If a lucky microphone is identified, then the audio signal output from that microphone 310 may be more heavily weighted or otherwise favored for generating the audio signal that drives speaker 320. The data extracted from the other less lucky microphones 310 may still be analyzed and used for other processing functions, such as localization.

In one embodiment, the processing performed by compute module 325 may preserve the user's natural HRTF thereby preserving their ability to localize the physical direction from where the original environmental sounds originated. In other words, the user will be able to identify the directional source of sounds originating in their environment despite the fact that the user is hearing a regenerated version of those sounds emitted from speaker 320. The sounds emitted from speaker 320 recreate the spaciousness of the original environmental sounds in a way that the user's mind is able to faithfully localize the sounds in their environment. In one embodiment, reinforcement of the natural HRTF is a calibrated feature implemented using machine learning techniques and trained neural networks.

Figure 5A:
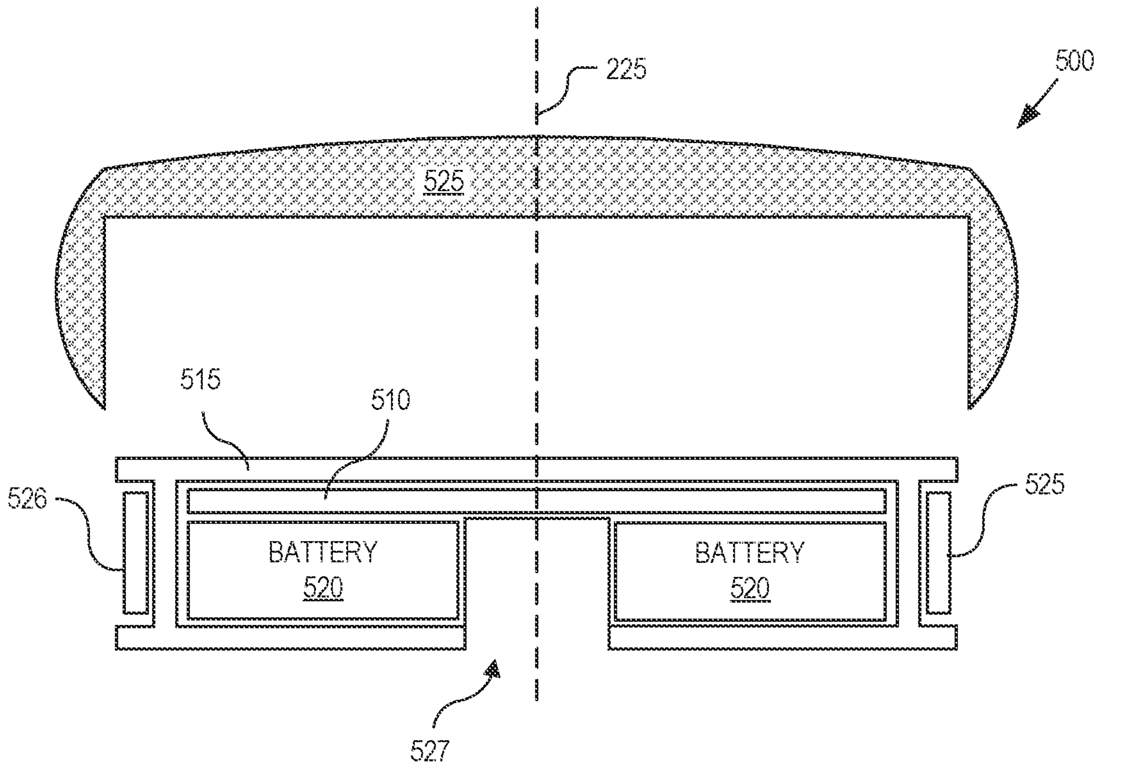
FIGS. 5A & 5B illustrate an electronics package of the ear-mountable listening device including an array of microphones disposed in a ring pattern around a main circuit board, in accordance with an embodiment of the disclosure.
Figure 5B:
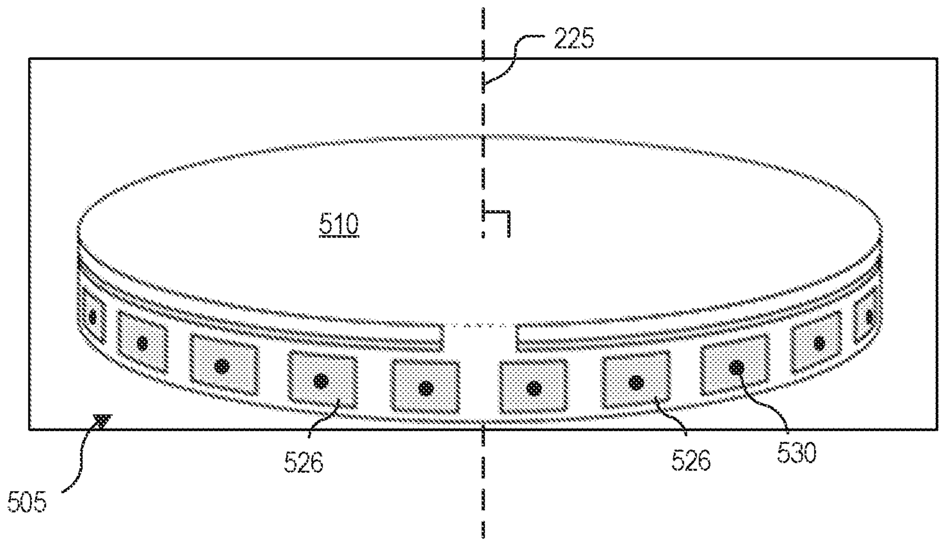

FIGS. 5A & 5B illustrate an electronics package 500, in accordance with an embodiment of the disclosure. Electronics package 500 represents an example internal physical structure implementation of electronics package 205 illustrated in FIG. 2. FIG. 5A is a cross-sectional illustration of electronics package 500 while FIG. 5B is a perspective view illustration of the same excluding cover 525. The illustrated embodiment of electronics package 500 includes an array 505 of microphones, a main circuit board 510, a housing or frame 515, a cover 525, and a rotary port 527. Each microphone within array 505 is disposed on an individual microphone substrate 526 and includes a microphone port 530.

FIGS. 5A & 5B illustrate how array 505 extends around central axial axis 225. Additionally, in the illustrated embodiment, array 505 extends around a perimeter of main circuit board 510. Although not illustrated, main circuit board 510 includes electronics disposed thereon, such as compute module 325, memory 330, sensors 335, communication circuitry 345, and interface circuitry 350. Main circuit board 510 is illustrated as a solid disc having a circular shape; however, in other embodiments, main circuit board 510 may be an annular disk with a central hole through which post 220 extends to accommodate protrusion of acoustic drivers aligned with the ear canal entrance. In the illustrated embodiment, the surface normal of main circuit board 510 is parallel to and aligned with central axial axis 225 about which the ring pattern of array 505 extends.

The electronics may be disposed on one side, or even both sides, of main circuit board 510 to maximize the available real estate. Housing 515 provides a rigid mechanical frame to which the other components are attached. Cover 525 slides over the top of housing 515 to enclose and protect the internal components. In one embodiment, a capacitive touch sensor is disposed on housing 515 beneath cover 525 and coupled to the electronics on main circuit board 510. Cover 525 may be implemented as a mesh material that permits acoustical waves to pass unimpeded and is made of a material that is compatible with capacitive touch sensors (e.g., non-conductive dielectric material).

Figure 6:
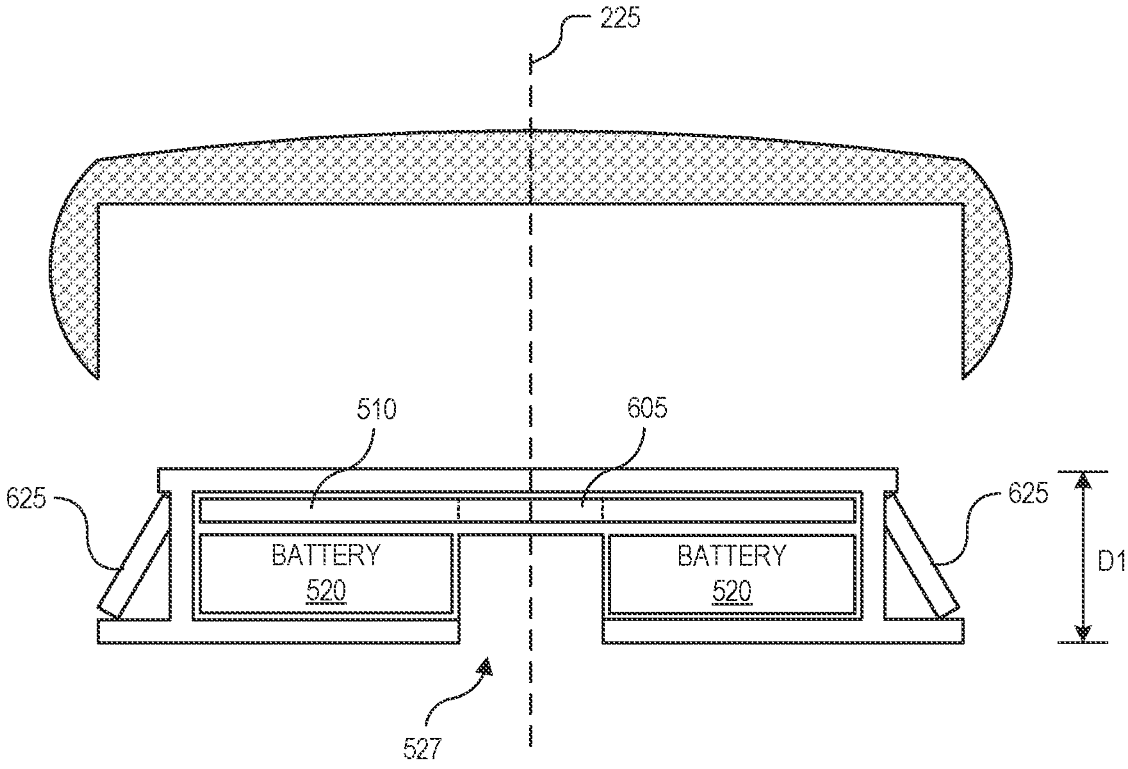
FIG. 6 is a cross-sectional illustration of an electronics package having tilted individual microphone substrates, in accordance with an embodiment of the disclosure.

As illustrated in FIGS. 5A & 5B, array 505 encircles a perimeter of main circuit board 510 with each microphone disposed on an individual microphone substrate 526. In the illustrated embodiment, microphone ports 530 are spaced in substantially equal angular increments about central axial axis 225. Of course, other nonequal spacings may also be implemented. The individual microphone substrate 526 are planer substrates oriented vertical (in the figure) or perpendicular to main circuit board 510 and parallel with central axial axis 225. However, in other embodiments, the individual microphone substrates may be tilted relative to central axial axis 225 and the normal of main circuit board 510 (see FIG. 6). As illustrated in FIG. 6, individual microphone substrates 625 are disposed along a conical plane around a perimeter of main circuit board 510. Tilting individual microphone substrates 625 permits a thinner profile (dimension D1) for electronics package 205, which may be perceived to have improved industrial design. Of course, the microphone array may assume other positions and/or orientations within electronics package 205.

FIG. 5A illustrates an embodiment where main circuit board 510 is a solid disc without a central hole. In that embodiment, post 220 of acoustic package 210 extends into rotary port 527, but does not extend through main circuit board 510. The inside surface of rotary port 527 may include magnets for holding acoustic package 210 therein and conductive contacts for making electrical connections to electrical trace rings 230. Of course, in other embodiments such as illustrated in FIG. 6, main circuit board 510 may be an annulus with a center hole 605 allowing post 230 to extend further into electronics package 205 enabling thinner profile designs for dimension D1. The center hole in main circuit board 510 provides additional room or depth for larger acoustic drivers within post 220 of acoustic package 205 to be aligned directly in front of the entrance to the user's ear canal.

Figure 7A:
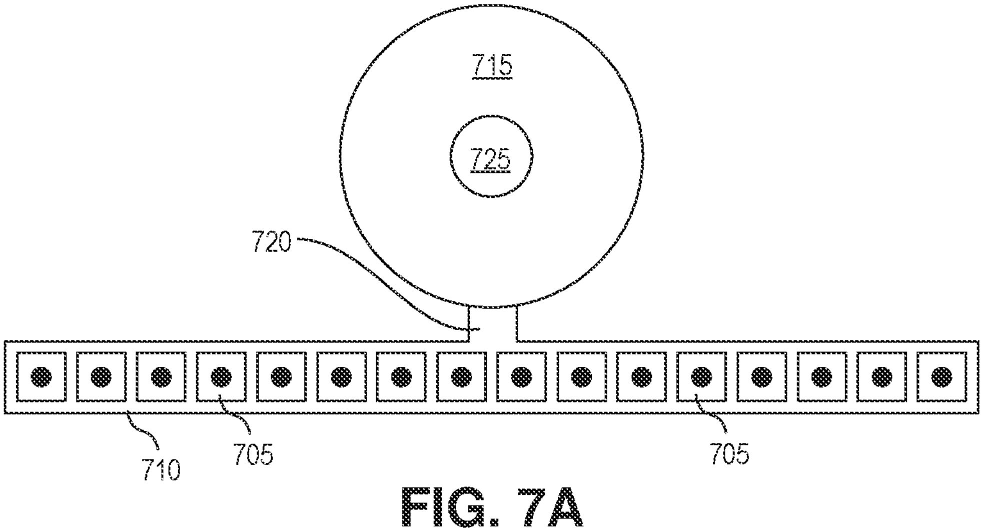
FIGS. 7A and 7B illustrate individual microphone substrates interlinked into the ring pattern via a flexible circumferential ribbon that encircles the main circuit board, in accordance with an embodiment of the disclosure.
Figure 7B:
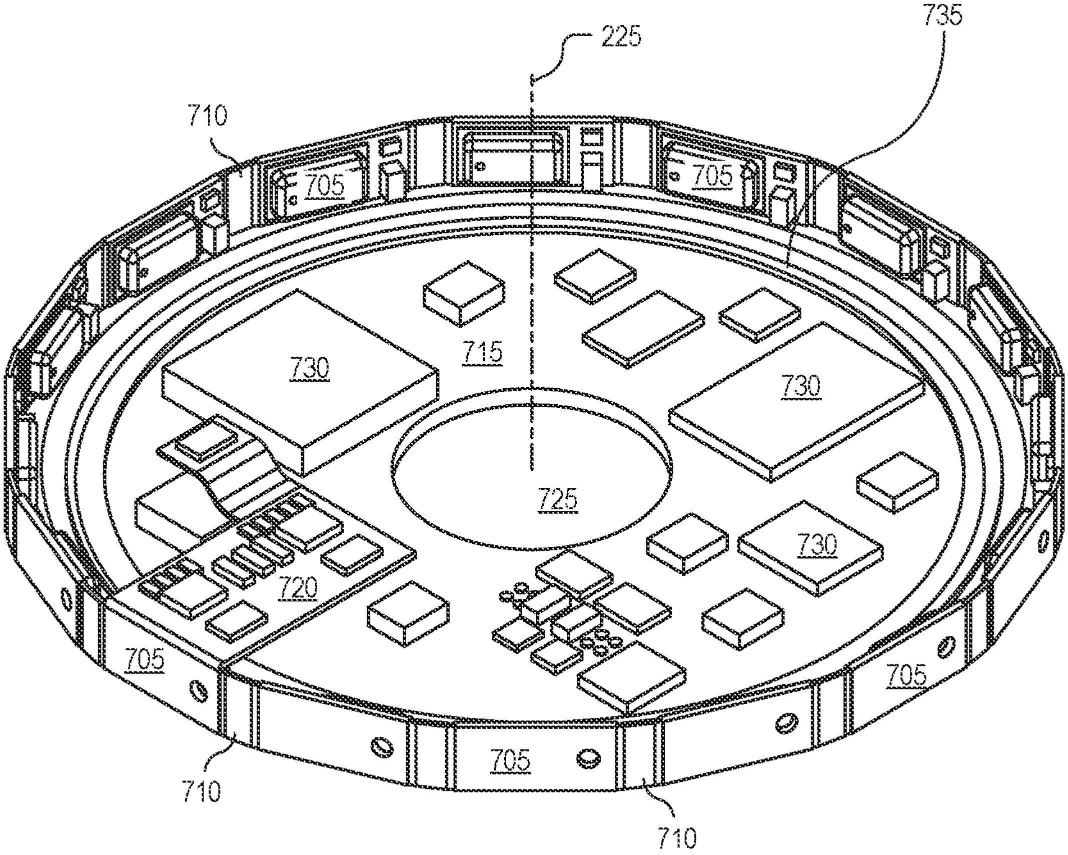

FIGS. 7A and 7B illustrate individual microphone substrates 705 interlinked into a ring pattern via a flexible circumferential ribbon 710 that encircles a main circuit board 715, in accordance with an embodiment of the disclosure. FIGS. 7A and 7B illustrate one possible implementation of some of the internal components of electronics package 205 or 500. As illustrated in FIG. 7A, individual microphone substrates 705 may be mounted onto flexible circumferential ribbon 710 while rolled out flat. A connection tab 720 provides the data and power connections to the electronics on main circuit board 715. After assembling and mounting individual microphone substrates 705 onto ribbon 710, it is flexed into its circumferential position extending around main circuit board 715, as illustrated in FIG. 7B. As an example, main circuit board 715 is illustrated as an annulus with a center hole 725 to accept post 220 (or component protrusions therefrom). Furthermore, the individual electronic chips 730 (only a portion are labeled) and perimeter ring antenna 735 for near field communications are illustrated merely as demonstrative implementations.

Figure 8:
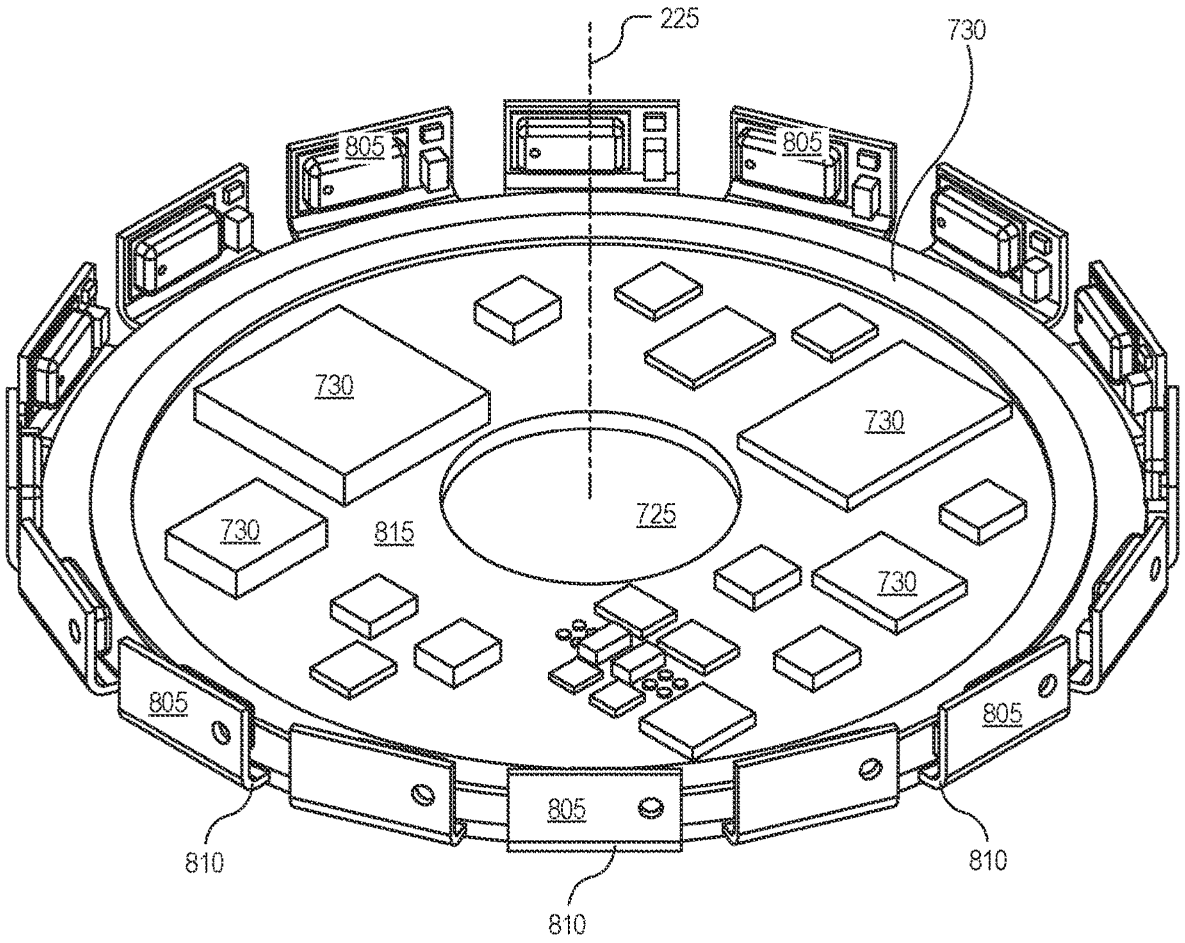
FIG. 8 illustrates individual microphone substrates linked to the main circuit board via flexible radial tabs extending from the main circuit board, in accordance with an embodiment of the disclosure.

FIG. 8 illustrates individual microphone substrates 805 linked to a main circuit board 815 via flexible radial tabs 810 extending radially from main circuit board 815 about a perimeter of main circuit board 815, in accordance with yet another possible implementation of electronics package 205 or 500. While individual microphone substrate 805 may be aligned parallel to central axial axis 225, the flexible radial tabs 810 also facilitate the tilted orientation illustrated in FIG. 6. Although FIGS. 7A, 7B, and 8 illustrate an array of 16 microphones, it should be appreciated that more or less microphones may be used.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ear-mountable listening device, comprising:

a circuit board;

an array of microphones physically arranged to encircle the circuit board to capture sounds from an environment, wherein each of the microphones of the array of microphones is configured to output one of a plurality of first audio signals that is representative of the sounds captured by a respective one of the microphones, wherein each of the microphones of the array of microphones is disposed on a corresponding one of a plurality of individual microphone substrates and the individual microphone substrates are linked to the circuit board;

a speaker arranged to emit audio into an ear in response to a second audio signal; and electronics disposed on the circuit board and coupled to the array of microphones and the speaker, the electronics including logic that when executed by the electronics causes the ear-mountable listening device to perform operations comprising:

capturing the sounds with the array of microphones to generate the first audio signals; and generating the second audio signal that drives the speaker based upon one or more of the first audio signals.

2. The ear-mountable listening device of claim 1, wherein the circuit board comprises an annular disk with a central hole and the speaker protrudes through the central hole.

3. The ear-mountable listening device of claim 1, wherein the array of microphones is arranged into a ring pattern extending around the circuit board.

4. The ear-mountable listening device of claim 3, wherein the ring pattern of the array of microphones and the circuit board share a central axial axis that substantially falls within a coronal plane of a user when the ear-mountable listening device is worn in the ear of the user.

5. The ear-mountable listening device of claim 4, wherein the speaker is positioned between an ear canal and the circuit board when the ear-mountable listing device is worn and the central axial axis, which is normal to the circuit board, passes through the speaker.

6. The ear-mountable listening device of claim 4, wherein microphone ports of the array of microphones are spaced in substantially equal angular increments about the central axial axis.

7. The ear-mountable listening device of claim 6, wherein the array of microphones includes at least sixteen independent microphones arranged into the ring pattern.

8. The ear-mountable listening device of claim 4, wherein each of the microphones of the array of microphones is disposed on a corresponding one of a plurality of individual microphone substrates that are planer and each tilted relative to the central axial axis.

9. The ear-mountable listening device of claim 1, wherein the individual microphone substrates are interlinked into a ring pattern via a flexible circumferential ribbon.

10. The ear-mountable listening device of claim 1, wherein the individual microphone substrates are linked to the circuit board via a flexible radial tab extending from the circuit board.

11. The ear-mountable listening device of claim 1, wherein the ear-mountable listening device includes three modular components comprising:

an electronics package having a puck-like shape and including the array of microphones and the electronics disposed therein;

a soft ear interface fabricated of a flexible material and having a shape to insert into a concha and an ear canal of the ear; and an acoustic package including the speaker, the acoustic package shaped to at least partially insert into the soft ear interface and connect the soft ear interface to the electronics package.

12. The ear-mountable listening device of claim 11, wherein the electronics package including the array of microphones is configured to align with a pinna plane of the ear when the ear-mountable listening device is worn.

13. The ear-mountable listening device of claim 11, wherein the electronics package rotates relative to the acoustic package to provide a rotary user interface with the ear-mountable listening device.

14. The ear-mountable listening device of claim 1, wherein the electronics includes further logic that when executed causes the ear-mountable listening device to perform further operations comprising:

capturing spatial information of the sounds incident upon the array of microphones; and reasserting a natural Head Related Transfer Function (HRTF) of a user with the audio emitted into the ear from the speaker to enable the user to localize origination of the sounds in the environment based upon the audio emitted from the speaker.

15. A modular ear-mountable listening system, comprising:

an acoustic package including a speaker arranged to emit audio into an ear when the modular ear-mountable listening system is worn in the ear; and an electronics package that removably couples to the acoustic package, the electronics package including:

a circuit board;

an array of microphones physically arranged to encircle the circuit board to capture sounds from an environment, wherein each of the microphones of the array of microphones is disposed on a corresponding one of a plurality of individual microphone substrates and the individual microphone substrates are linked to the circuit board; and electronics disposed on the circuit board and coupled to the array of microphones and the speaker, the electronics configured to receive first audio signals from the array of microphones and generate a second audio signal based upon one or more of the first audio signals for driving the speaker.

16. The modular ear-mountable listening system of claim 15, wherein the speaker of the acoustic package is positioned between an ear canal and the circuit board when the modular ear-mountable listing system is worn and a central axis of the circuit board that is normal to the circuit board passes through the speaker.

17. The modular ear-mountable listening system of claim 16, wherein the circuit board comprises an annular disk with a central hole, the central axis comprises a central axial axis, and at least part of the speaker protrudes through the central hole.

18. The modular ear-mountable listening device of claim 16, wherein the array of microphones is arranged in a ring pattern extending around the central axis and the central axis substantially falls within a coronal plane of a user when the modular ear-mountable listening system is worn in the ear of the user.

19. The modular ear-mountable listening system of claim 15, wherein the individual microphone substrates are interlinked into a ring pattern along a flexible circumferential ribbon.

20. The modular ear-mountable listening system of claim 15, wherein the individual microphone substrates are linked to the circuit board via a flexible radial tab extending from the circuit board.

21. The modular ear-mountable listening system of claim 15, wherein the electronics package rotates relative to the acoustic package to provide a rotary user interface and wherein the electronics package rotates relative to the acoustic package with a maximum number of detents that is related to a number of the microphones in the array of microphones to enable angular position disambiguation for each of the detents using acoustical beamforming with the array of microphones.

* * * * *